US009872795B2

(12) United States Patent
Laubach et al.

(10) Patent No.: US 9,872,795 B2
(45) Date of Patent: Jan. 23, 2018

(54) THERMOFORMABLE MEDICAL MEMBER WITH HEATER AND METHOD OF MANUFACTURING SAME

(71) Applicant: RECHARGEABLE BATTERY CORPORATION, College Station, TX (US)

(72) Inventors: Adam Laubach, Kingwood, TX (US); Alberto Macias Barrio, College Station, TX (US)

(73) Assignee: RECHARGEABLE BATTERY CORPORATION, College Station, TX (US)

( * ) Notice: Subject to any disclaimer, the term of this patent is extended or adjusted under 35 U.S.C. 154(b) by 500 days.

(21) Appl. No.: 14/482,351

(22) Filed: Sep. 10, 2014

(65) Prior Publication Data

US 2015/0257918 A1    Sep. 17, 2015

Related U.S. Application Data

(63) Continuation-in-part of application No. 14/206,252, filed on Mar. 12, 2014, now Pat. No. 9,642,736.

(51) Int. Cl.
| | |
|---|---|
| *A61F 5/00* | (2006.01) |
| *A61F 5/058* | (2006.01) |
| *B29C 51/42* | (2006.01) |
| *B29K 67/00* | (2006.01) |
| *B29L 31/00* | (2006.01) |

(52) U.S. Cl.
CPC ............ *A61F 5/058* (2013.01); *B29C 51/421* (2013.01); *B29K 2067/046* (2013.01); *B29K 2995/0013* (2013.01); *B29L 2031/753* (2013.01)

(58) Field of Classification Search
CPC . A61F 5/058; B29C 51/421; B29K 2067/046; B29K 2995/0013; B29L 2031/753
USPC ........................................................ 602/6–10
See application file for complete search history.

(56) References Cited

U.S. PATENT DOCUMENTS

| | | | |
|---|---|---|---|
| 4,874,656 | A | 10/1989 | Rantanen |
| 5,919,547 | A | 7/1999 | Kocher et al. |
| 7,722,782 | B2 | 5/2010 | Coffey et al. |
| 8,137,392 | B2 | 3/2012 | Friedensohn et al. |
| 2002/0077401 | A1 | 6/2002 | Chaudhary et al. |
| 2004/0006950 | A1 | 1/2004 | Knoerzer et al. |
| 2004/0042965 | A1 | 3/2004 | Usui et al. |
| 2004/0211698 | A1 | 10/2004 | Mak |
| 2007/0007229 | A1 | 1/2007 | Yousif |

(Continued)

OTHER PUBLICATIONS

Dellarocca, P.; "Air-Activated Ration Heaters;" Proceedings of the Army Science Conference (26th); dated Dec. 2008.

(Continued)

*Primary Examiner* — Ophelia A Hawthorne
*Assistant Examiner* — Caitlin Carreiro
(74) *Attorney, Agent, or Firm* — Schroeder Intellectual Property Law Group, LLC (57) ABSTRACT

A thermoformable medical member and heater and method for manufacturing same. A thermoplastic material is converted from a relatively rigid state to a formable state over a narrow temperature range, and, which reverts back to a clinically rigid state within a relatively short period of time, and, which remains in that state even at elevated ambient temperatures.

128 Claims, 5 Drawing Sheets

(56) References Cited

U.S. PATENT DOCUMENTS

| | | |
|---|---|---|
| 2007/0142883 A1 | 6/2007 | Quincy, III |
| 2007/0202284 A1 | 8/2007 | True |
| 2008/0154164 A1* | 6/2008 | Sheehan .................. A61F 5/01 602/7 |
| 2008/0202490 A1 | 8/2008 | Dodo |
| 2010/0163011 A1 | 7/2010 | Tinker et al. |
| 2010/0278454 A1 | 11/2010 | Huffer |
| 2010/0326418 A1 | 12/2010 | Sesock et al. |
| 2011/0081460 A1 | 4/2011 | Becraft et al. |
| 2011/0103718 A1 | 5/2011 | Bosman |
| 2011/0204054 A1 | 8/2011 | Huffer |
| 2012/0101417 A1* | 4/2012 | Joseph ..................... A61F 5/01 602/5 |
| 2012/0184672 A1* | 7/2012 | Riscanu .................. C08J 3/226 524/601 |
| 2013/0174835 A1 | 7/2013 | Tinker et al. |
| 2013/0345649 A1 | 12/2013 | Stockley, III et al. |

OTHER PUBLICATIONS

CookPak®—Self-Heating Packaging Technology for Food; RCE Technologies; dated Aug. 21, 2013.

Exothermic Nanocomposite for Self-Contained Ration Heater; U.S Army NSRDEC—NNI Scientific Accomplishments; dated 2009.

"U.S. Market for Packaging Barrier Resins to Reach 8.6 Billion Pounds by 2009" [online] [retrieved Mar. 17, 2015]. Retrieved from the internet: <URL: http://www.ien.com/article/us-market-packaging/8562>. 6 pages.

International Search Report and Written Opinion in International Application No. PCT/US2015/020150 dated Jun. 12, 2015, 10 pages.

International Search Report and Written Opinion in related International Application No. PCT/US2015/020153 dated Jun. 18, 2015, 11 pages.

Unpublished U.S. Appl. No. 14/206,252, filed Mar. 12, 2014 to Laubach et al.

\* cited by examiner

Side View     Top View

FIG. 9

THERMOFORMABLE MEDICAL MEMBER WITH HEATER AND METHOD OF MANUFACTURING SAME

CROSS REFERENCE TO RELATED APPLICATIONS

The present invention is a continuation-in-part of Co-pending application Ser. No. 14/206,252, filed on Mar. 12, 2014, the entirety of which is incorporated herein by reference.

FIELD OF THE INVENTION

The invention relates to a portable thermoformable medical member in association with a heater that generates heat from an exothermic reaction.

BACKGROUND OF THE INVENTION

Thermoformable materials have been used in association with medical structures such as casts, splints, orthotics, etc., for medical purposes for several years. Indeed, such materials offer several benefits over conventional non-thermoformable materials such as faster set times, eliminating the lengthy application process associated therewith and the dampness inflicted on the patients skin.

U.S. Pat. No. 4,778,717 is directed to a specific structure for a thermoplastic, thermoformable composite.

U.S. Pat. No. 5,652,053 discloses utilizing a molecular or intermolecular combination of materials comprised of an inter-penetrating polymer network so as to cause the combined structure to transfer from an amorphous state to a viscoelastic and rubbery state. While such a structure may provide some support to a user, it is not effective when a ridged support is desired such as is typically the case with a splint, cast, orthotic or exoskeleton.

U.S. Pat App. Nos. 20080319362 and 20120101417 both disclose a thermoformable cast or splint that can be used in association with an exothermic heating reaction for causing a thermoplastic material to go from a relatively rigid state to a malleable state so that the material can be formed to a portion of a patient in need of support. Unfortunately, in order to heat the thermoplastic material in such a reaction, the material is placed in a separate and distinct heating bag where the exothermic reaction takes place. After appropriate heating, the thermoplastic material is removed from the bag and ready for use.

In addition, the assignee of the present invention has provided oxygen-based heaters and various packages for same. See, e.g., U.S. Pat. No. 7,722,782, issued on May 25, 2010; U.S. application Ser. No. 12/376,927, filed on Feb. 9, 2009; U.S. application Ser. No. 12/874,338, filed on Sep. 2, 2010; U.S. application Ser. No. 14/055,250 filed on Oct. 16, 2013; U.S. application Ser. No. 14/058,719, filed on Oct. 21, 2013; U.S. application Ser. No. 14/058,496, filed on Oct. 21, 2013; and, U.S. Ser. No. 13/734,594, filed Jan. 4, 2013, all of which are incorporated herein by reference.

These disclosed heaters and packages are successful at providing an oxygen based heater and/or package for same.

While the above disclosed devices and methods may be capable of providing effective formable medical structures, none of them disclose such a device that provides for the conversion of a thermoformable material from a relatively rigid state to a formable state over a narrow temperature range, and, which reverts back to a clinically rigid state within a relatively short period of time, and, which remains in that state even at elevated ambient temperatures. The present invention is provided to solve these and other problems.

SUMMARY OF THE INVENTION

The present invention is directed to a thermoformable medical member and heater comprising a thermoplastic material having a top side and a bottom side opposite the top side. The thermoplastic material comprises a flexural modulus at 73 degrees F. of at least 2.3 GPa, a heat deflection temperature less than 70 degrees C.; and a thermoformable temperature in the range of 35-70 degrees C. In addition, a heater is operatively associated with at least one of the top and bottom sides of the thermoplastic material.

In a preferred embodiment of the invention, the thermoplastic material has a tensile modulus of at least 0.3 GPa at 23 degrees C.

In this embodiment, the thermoplastic material contains a polylactic acid (PLA) polymer, cellulose acetate butyrate, or polycaprolactone. In addition, the PLA polymer has a flexural modulus of 2.4-4.9 GPa at 23 degrees C. Also, the PLA polymer has an L-lactide/D-lactide ratio of 24:1 to 30:1.

In yet another preferred embodiment the thermoplastic material includes at least one of an organic and inorganic filler. It is contemplated that the filler has a thermal conductivity greater than 0.12 W/(meter ° C.) at 48 degrees C.

In still another preferred embodiment of the invention, the thermoplastic material has at least a portion of at least one of the top and bottom sides with a textured surface. For example, the textured surface may be corrugated.

In one preferred embodiment of the invention, the thermoplastic material has an internal structure, having a volume, located between the top and bottom sides, wherein 40% or less of the volume is defined by an open cell structure. This internal structure may take the form of a honeycomb configuration.

In the preferred embodiment of the invention, the thermoformable medical member comprises at least one of a splint, cast, an orthotic or an exoskeleton member.

In yet another preferred embodiment of the invention, the heater comprises either an oxygen activated heater or a water activated heater. It is preferred, but not required, that the heater is integrated with the thermoformable medical member. Such integration may take the form of the thermoplastic material being chemically or physically bonded to the heater.

In a preferred embodiment of the invention, the thermoplastic material has a glass transition temperature in the range of 35-70 degrees C. In addition, the thermoplastic material contains a reinforcing fiber.

In the preferred embodiment of the invention, the thermoformable medical member contains a thermosetting component capable of forming crosslinks in the range of 20-70 degrees C.

The present invention is also directed to a method for achieving an effect on a thermoformable medical member from a heater for use on a patient comprising the steps of: heating a thermoformable medical member fabricated from a thermoplastic material with at least one of an oxygen activated heater and a water activated heater in a range of 48-70 degrees C., wherein the thermoplastic material prior to heating is in a relatively rigid, non-thermoformable phase; converting the thermoplastic material from a non-thermoformable state to a thermoformable state within the heated range; forming the thermoplastic material to a desired shape while in its thermoformable state; converting the thermoplastic material back toward and into a relatively rigid non-thermoformable phase; and maintaining the desired shape of the thermoplastic material at a temperature imparted to the thermoplastic material of less than 48 degrees C.

In the preferred method, the step of converting the thermoplastic material from a non-thermoformable state comprises maintaining structural rigidity of the thermoplastic material until the thermoplastic material until it is heated within the range of 48-70 degrees C.

In this preferred method the step of heating comprises constructing the heater so that it ceases to generate heat to the thermoplastic material in the range of 48-70 degrees C. after the thermoplastic material has been converted to a thermoformable state. It is preferred that the thermoformable state is maintained for approximately 1-7 minutes, and, preferably 3-5 minutes.

In this preferred embodiment, the step of converting the thermoplastic material back toward and into a relatively rigid non-thermoformable state occurs after the temperature of the thermoplastic material is less than 48 degrees C. Again, this occurs within 1-7 minutes, and, preferably 3-5 minutes.

DETAILED DESCRIPTION OF THE DRAWINGS

The present, disclosure and the various features and advantageous details thereof are explained more fully with reference to the non-limiting embodiments and examples that are described and/or illustrated in the accompanying drawings and detailed in the following description. It should be noted that the features illustrated in the drawings are not drawn to scale, and features of one embodiment may be employed with other embodiments, as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the invention may be practiced and to further enable those of skill in the art to practice the examples of the disclosure. Accordingly, the examples and embodiments herein should not be construed as limiting the scope of the invention.

Figure 1:
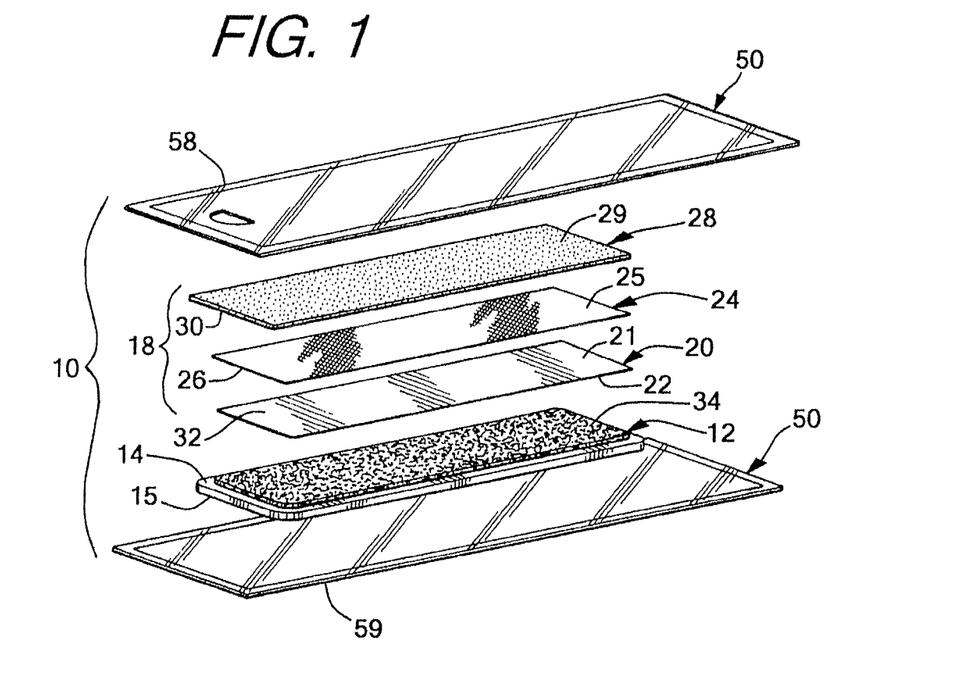
FIG. 1 of the drawings is an exploded view of the present invention.

Thermoformable medical member and heater 10 is shown in FIG. 1 as comprising thermoplastic material 12 and oxygen activated heater 18. Thermoplastic material 12, which, in this embodiment, will result in a formable and rigid splint, has top side 14 and bottom side 15. As will be explained in greater detail, the thermoplastic material becomes malleable ("formable") upon heating to a predetermined temperature (48-70 degrees C.), which is a relatively narrow temperature range as compared to known thermoformable splint materials. As will also be explained, the thermoplastic material will revert back toward and into a clinically rigid state at a temperature below 48 degrees C. Accordingly, once the thermoplastic material is formed to a desired shape, it will maintain that shape, and, in turn, its clinically rigid state, even at elevated ambient temperatures. As will be understood to those having ordinary skill in the art, the term "clinically rigid state" means that the splint will maintain its desired shape without softening and/or deforming after it has been formed by the person applying the material/member to a patient.

In the preferred embodiment of the invention, the thermoplastic material is constructed so that it has a flexural modulus at 23 degrees C. of approximately 2.4-4.9 GPa, a heat deflection temperature less than 70 degrees C., and, a thermoformable ("malleable") temperature in the range of 48-70 degrees C. It is also contemplated that the thermoplastic material has a tensile modulus of at least 0.3 GPa at 23 degrees C. It is contemplated that the thermoplastic material contains a polyactic acid ("PLA") polymer. The PLA has an L-lactide/D-lactide ratio of 24:1 to 30:1. As would be appreciated by those having ordinary skill in the art, although the thermoplastic material has been identified as containing PLA, other materials that will exhibit similar properties under similar pressures and temperatures are also contemplated by the present invention. Examples include cellulose acetate butyrate or polycaprolactone. Indeed, it is contemplated that other materials can be combined with, for example, the PLA, such other materials include, but are not limited to, lower durometer plastics such as EVA. Of primary concern is the relatively narrow temperature range in which the thermoplastic material becomes formable, the time of formability (as will be further explained), and, being able to maintain a clinically rigid state after the thermoformable member has been properly formed, even at temperatures below 120 degrees F.

Thermoplastic material 12 may further include at least one organic or inorganic filler for reducing the overall cost and for improving the mechanical properties (i.e. flexural modulus) of the device. The filler has a thermal conductivity greater than 0.12 W/(meter degrees C.) at 48 degrees C.

Figure 6:
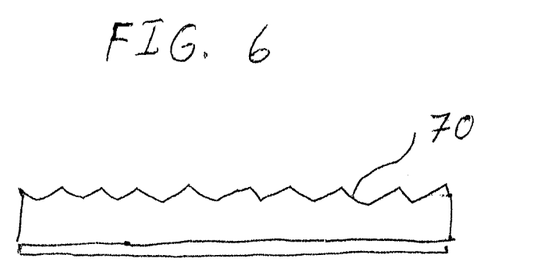
FIG. 6 of the drawings is a side view of one of the features of the present invention.
Figure 7:
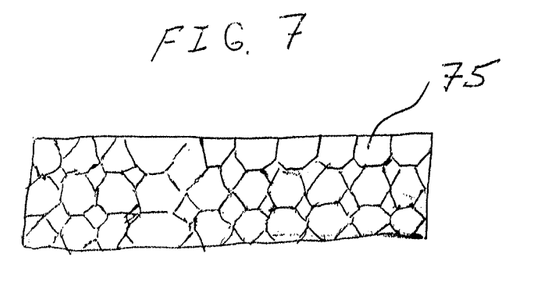
FIG. 7 is a top view of one of the features of the present invention.

Thermoplastic material 12 is shown in FIGS. 6 and 7 as including a corrugated surface 70 (FIG. 6) and an open cell configuration 75 (FIG. 7). The corrugated surface maximizes physical contact between thermoplastic material 12 and oxygen activated heater 18. The open cell configuration (such as a honeycomb configuration) helps to maximize heat transfer between the heater sheet and the thermoplastic material. It is contemplated that the thermoplastic material is occupied by 40% or less than the open cell configuration. Although a corrugated surface and an open cell configuration have been disclosed, it will be understood by those have ordinary skill in the art that other configurations can be used for optimizing/increasing heat transfer from the heater to the thermoplastic material.

Oxygen activated heater 18 includes heater sheet 20, wicking layer 24 and air diffuser layer 28. Heater sheet 20, wicking layer 24 and air diffuser layer 28 each have a top surface and a bottom surface 21 and 22, 25 and 26, and, 29 and 30, respectively. The heater sheet comprises a metal-based substrate that exothermically reacts with and upon exposure to oxygen. Although the heater sheet is identified as a "sheet" or "substrate", it is contemplated by the present invention that the heater sheet can actually be applied as a layer, such as by deposition coating, rolling of material, etc.

Examples of the chemistry and general mechanical configurations associated with oxygen activated heaters are known in the art and specific examples have been incorporated herein by reference in the Background of the Invention. As will be readily understood by those having ordinary skill in the art with such heaters, wicking layer 24 serves to distribute the electrolyte evenly into the heater sheet. This electrolyte facilitates the reaction that takes place when the heater sheet is exposed to oxygen.

Figure 2:
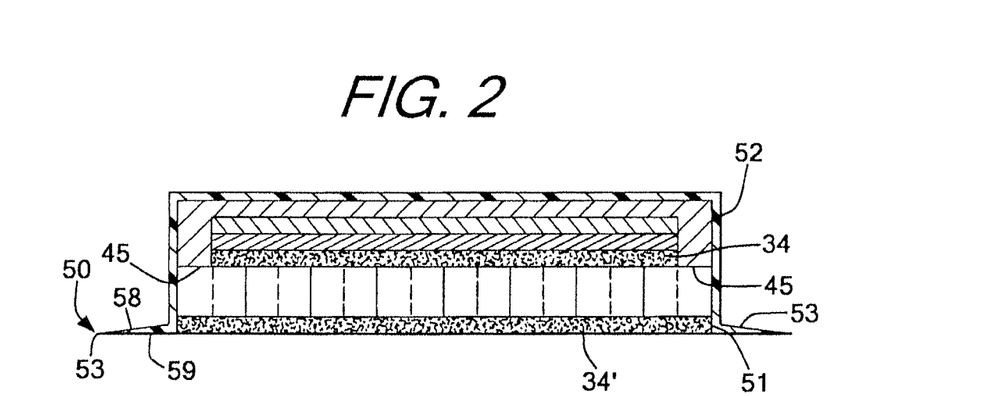
FIG. 2 of the drawings is an elevated cut-away view of the present invention.
Figure 3:
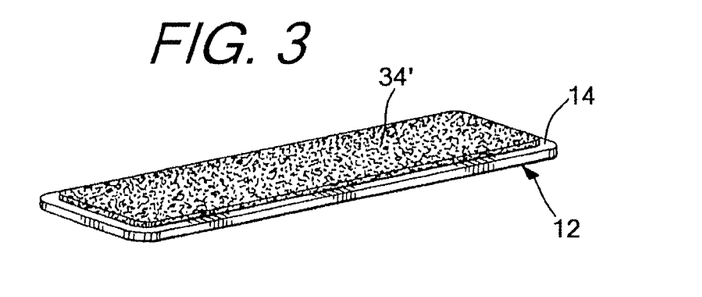
FIG. 3 of the drawings is a top perspective view of one of the features of the present invention.
Figure 5:
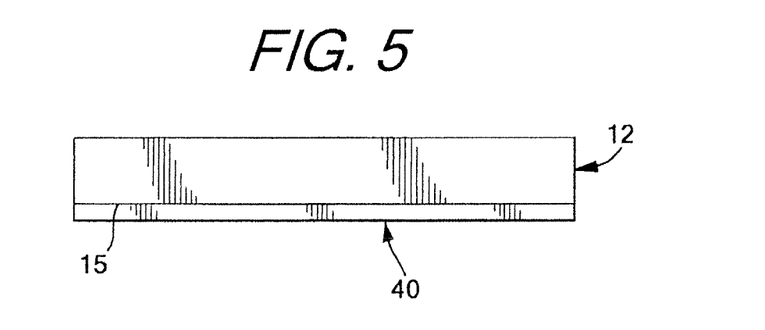
FIG. 5 of the drawings is an elevated side view of one of the features of the present invention.

As shown in greater detail in FIG. 2 (but as is also apparent in FIG. 1), bottom surface 22 of heater sheet 20 is operatively associated with top side 14 of thermoplastic material 12. Such association can occur as a result of chemical or mechanical bonding there between, or a combination thereof. For example, as shown in FIG. 1, top side of thermoplastic material 12 is associated with binding component 34. In this embodiment, the binding component comprises a non-woven fabric secured to the thermoplastic material. Although a non-woven fabric has been disclosed, other binding components are also contemplated by the present invention, including, but not limited to, adhesive materials, such as glue and double sided thermal tape. (See, for example, double sided thermal tape 34, shown in FIG. 3). In addition to the felt acting as a binding agent, desired felt may also include some heat insulating properties. Accordingly, it is contemplated that such felt, or other heat insulating material 40 (see FIG. 5) also be associated with bottom side 15 of thermoplastic material 12 inasmuch as the bottom side will be the side that comes into contact with the skin of a patient. Heat insulating material 40 in FIG. 5 can serve as a resilient pad, known as a cast pad, and is placed on bottom side 15 of thermoplastic material 12 for providing thermal protection while thermoformable medical member and heater 10 are being formed to the appropriate region of a patient, as well as providing comfort to the wearer after the thermoplastic heater reverts from a malleable state back to a relatively rigid state.

As can be seen in FIGS. 1 and 2, bottom surface 26 of wicking layer 24 is operatively associated with and over top surface 21 of the heater sheet. Additionally, bottom surface 30 of air diffuser layer 28 is operatively positioned over top surface 25 of the wicking layer. As shown in FIG. 2, air diffuser layer (which allows relatively uniform dispersion of oxygen toward and in contact with the wicking layer, and, in turn, the heater sheet upon association with oxygen) includes peripheral region 45 as a result of it having a length and width greater than the length and width of the wicking layer and heater sheet. Accordingly, peripheral region 45 of air diffuser layer 28 is adhered to a portion of the top side of thermoplastic material 12. Such adherence secures/contains the heater sheet and wicking layer in operative association with the thermoplastic material. Although the diffuser layer and the wicking layer have been described as two separate components, it is also contemplated that those two layers be combined into a single unitary structure. Alternatively, it is also contemplated that one material can achieve the function of both of those layers.

As shown in FIGS. 1 and 2, thermoformable medical member and heater 10 further includes outer housing 50. The outer housing, once assembled about oxygen activated heater 18 and thermoplastic material 12, includes interior region 51 and outer surface 52 (see FIG. 2). As can be seen in FIG. 2, such an assembly is completely positioned within the interior region of the outer housing. As shown in FIGS. 1 and 2, outer housing 50 includes first and second sheets of material 58, 59, respectively. The first and second sheets of material are adhered at their edges (see FIG. 2) so as to form seal 53. The outer housing is fabricated from a material that is relatively impervious to oxygen transmission. One example of acceptable material for the outer housing is commercially available from Curwood Inc. P.O. Box 2968, 2200 Badger Ave., Osjkosh, Wis. 54903 under the trade name Liquiflex® A6661-MO. Seal 53 also is relatively impervious to oxygen transmission.

Figure 4:
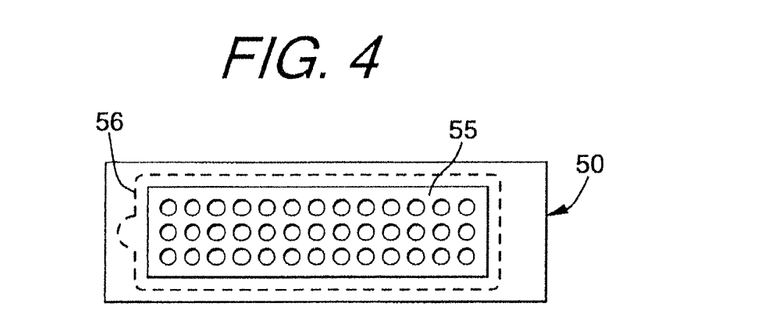
FIG. 4 of the drawings is a top view of one of the features of the present invention.

Outer housing 50 may include oxygen penetration region 55 and removable seal 56 operatively positioned over and around the oxygen penetration region, as shown in FIG. 4. The oxygen penetration region includes pores, or sections that will allow oxygen transmission into interior region 51 of the outer housing. However, removable seal 56 is comprised of a material (that may be the same as the material used for outer housing 50) that is intended to precluded oxygen transmission there through. Accordingly, oxygen will be precluded from entering interior region of the housing unless and until the removable seal is at least partially removed. Although outer housing has been described with an oxygen penetration region, it is also contemplated that such a region not be used. In such a case, oxygen will only be transmitted to the oxygen activated heater upon physical removal of the integrated heater and thermoplastic material from interior region 51 of the outer housing.

Thermoformable medical member and heater 10 is manufactured by fabricating oxygen activated heater 18 with air diffuser layer 28, wicking layer 24 and a metal-based (such as zinc) heater substrate 20, and securing all of them to thermoplastic material 12. As previously explained, the heater sheet is adhered to the thermoplastic material by means of a chemical and/or mechanical bond, such as with non-woven felt or an adhesive applied to top side 14 of the thermoplastic material. In addition, cast pad 40 (FIG. 5) may be applied to bottom side 15 of the thermoplastic material for thermal protection and comfort. As also previously explained, the air diffuser layer includes a peripheral region 45 that extends beyond the peripheries of the wicking layer and heating sheet. Inasmuch as the thermoplastic material has a length and width that is also greater than that of the wicking layer and heating sheet, the peripheral region 45 of the air diffuser layer can be secured to a portion of the thermoplastic material (see FIG. 2). In this instance, the heater sheet is held against the thermoplastic material by being "sandwiched" between the air diffuser and the thermoplastic material, and direct binding of the heater sheet to the thermoplastic material may not be required.

An outer housing 50 is fabricated from a flexible material that is relatively impermeable to oxygen. The outer housing is constructed to have a top sheet 58 and bottom sheet 59. Once constructed, the combined and integrated oxygen activated heater 18 (FIG. 1) and thermoplastic material 12 are positioned within what will become interior region 51 (FIG. 2) of the outer housing. The top and bottom sheet of the outer housing are then sealed together, optionally under a vacuum, forming seal 53 so that the interior region of the outer housing is substantially devoid of oxygen, and wherein the outer housing substantially conforms around the thermoplastic material and oxygen activated heater.

As an alternative embodiment, top sheet 58 of the outer housing can be fabricated with pores, or oxygen penetration regions 55, and a removable seal 56 positioned there over. As previously described, in such an embodiment, oxygen will only transmit into the interior region of the outer housing upon at least partial removal of the removable seal.

Figure 8:
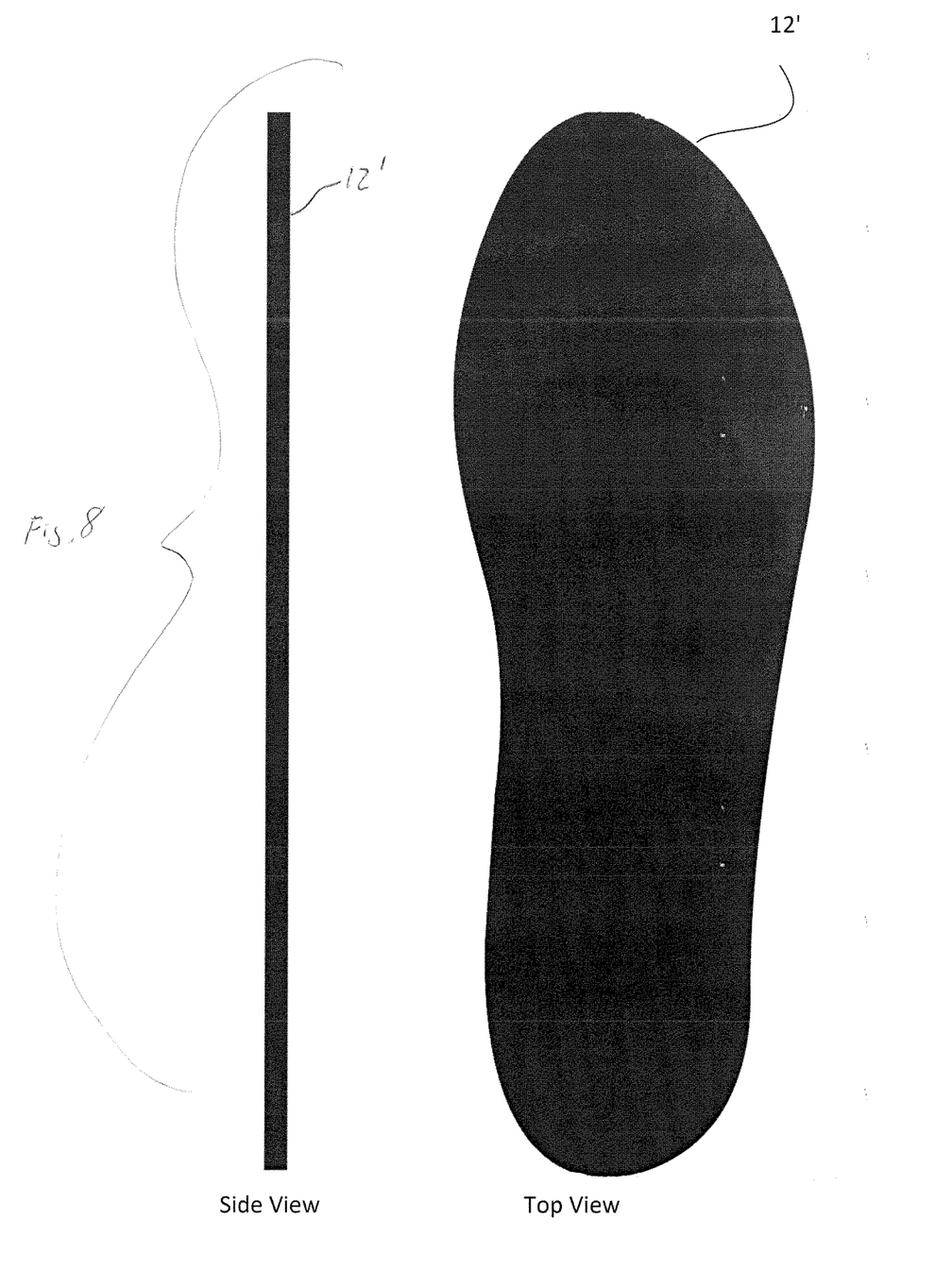
FIG. 8 is a perspective view of orthotic devices of the present invention.

Although thermoformable medical member and heater 10 have been described/shown in FIGS. 1 and 2 as a splint having an integrated oxygen activated heater, such is for disclosure and understanding of the invention only. Indeed, as shown in FIG. 8, thermoplastic material 12' is shown as comprising orthotic devices. In addition, it will be readily understood to those with ordinary skill in the art that the present invention is equally applicable to exoskeleton devices. Examples of exoskeleton devices contemplated by the present invention includes, but are not limited to, prosthetics, braces and sports armour.

As will be readily apparent to those having ordinary skill in the art, other thermoformable medical members can also be used in association with the teachings of the present invention. In addition, although the heater has been disclosed as comprising an oxygen activated heater integrally associated with the thermoplastic material, other heaters that generate heat as a result of an exothermic reaction are also contemplated—such as various conventional water activated heaters. Furthermore, in some applications it may be beneficial to have the heater as a separate, non-integrated component relative to the thermoplastic material. In such a case, operative association of the heater with the thermoplastic material would occur at the time of intended formation/molding.

In operation, (and as will be described with respect to an integrated oxygen activated heater) a desired user of the thermoformable medical member and heater would merely open the outer housing (by, for example, cutting a sealed edge with a scissors, or by tearing at a perforated line) and then removing the integrated thermoplastic material and oxygen activated heater there from. (Prior to commencement of heating, the thermoplastic material will be in a relatively rigid state). As oxygen from the ambient environment comes into contact with the air diffuser layer, and, in turn, into contact with the wicking layer, a chemical reaction will occur causing the heater sheet to create an exothermic reaction. This exothermic reaction will result in the release of heat from the heater sheet toward and into the thermoplastic material to a temperature range of 48-70 degrees C. This temperature range will be maintained for a predefined period of time (typically 3-5 minutes) at which point the thermoplastic material will become and remain malleable/formable for a predetermined period of time. It will be understood that the amount of time the thermoplastic material stays in the malleable state is a function of how long heat in the previously identified temperature range is imparted into the thermoplastic material. How to alter this time would be readily understood to those having ordinary skill in the art merely by altering the amount of active material associated with producing the desired exothermic reaction associated with the heater.

Once the thermoplastic material is in a formable state, a person would then place the device onto a person's arm (for example) and press the thermoplastic material against the person's arm until it forms thereto. Once properly formed, an elastic bandage, or the like, is wrapped around the person's arm and the thermoplastic material and oxygen activated heater (when integrated) so as to secure it in place. Inasmuch as the side of the thermoplastic material applied to the person's arm may include an insulating pad (such as a cast pad) he or she will not be subjected to unsafe temperatures. The air diffuser layer also has heat insulating properties, so the person applying the device will also be protected from unsafe temperatures.

As previously mentioned, after the thermoplastic splint has become malleable, it will continue in that state until the temperature of the thermoplastic material drops below 48 degrees C. In a preferred embodiment of the method, the time it remains malleable, and, in turn "workable", is about one minute. After that, the thermoplastic material, and, in turn, the splint, will be in a clinically rigid and formed state. Such a quick time before reverting to a non-formable state greatly reduces the amount of time before the limb, or the like, is properly secured and stabilized. Again, this time can be altered by increasing the amount of time the exothermic reaction continues at the previously identified temperatures. Those with ordinary skill in the art will readily recognize that other thermoformable medical members, such as orthotics and exoskeleton devices can likewise be formed in accordance with the teachings of the present invention—with or without an integrated heater, depending on the particular application.

Figure 9:
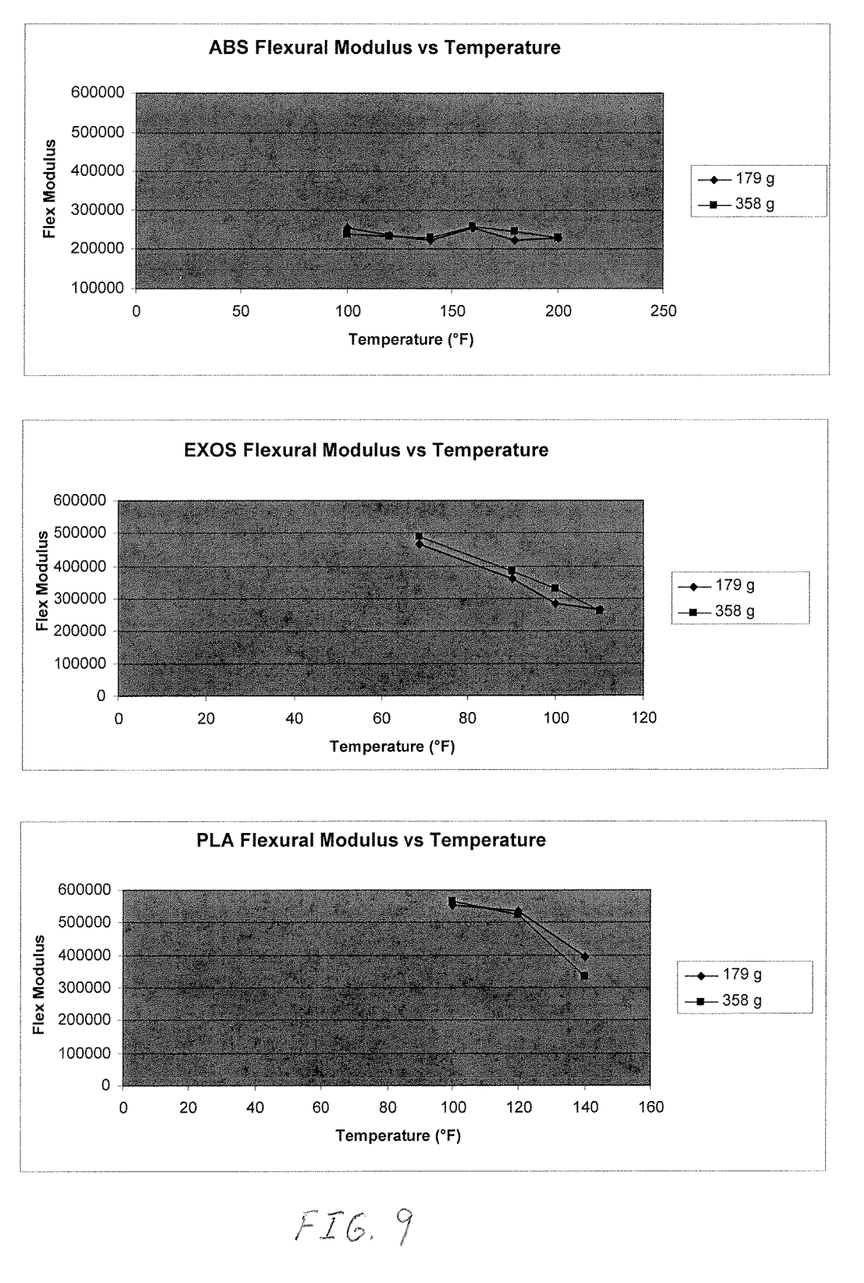
FIG. 9 is three graphical representations of experimental results. Flexural moduli were calculated at room temperature for loadings of 0.396 and 0.789 pounds.

In support of the above, experiments were conducted using three different thermoformable (thermoplastics) materials: Acrylonitrile Butadiene Styrene ("ABS"); an unknown material used by DJO Global of Vista, Calif. for thermoformable splints sold under the trademark EXOS ("EXOS"); and, a PLA in accordance with the present invention ("PLA"). In these experiments, the three materials were each spaced 6 inches apart and tested for deflection under controlled loads at seven different temperatures. Specifically, each of the materials were placed on two triangular prisms. A drop gauge was fitted with an approximately 179 g weight and then allowed to drop on the center of the respective material at each of the different temperatures. The tests were repeated with an approximately 358 g weight. Deflection of each of the materials was read and recorded based on the readings from the drop gauge. The results of those tests can be seen in graphical form in combined FIG. 9—revealing flexural modulus (psi) vs. temperature in degrees F.

As can be seen from the graphs in FIG. 8, the flexural modulus of the ABS had insignificant change at temperatures from ambient to 200 degrees F. The EXOS material softened significantly between 70 and 100 degrees F. (temperatures often experienced in the ambient environment). Indeed, the EXOS material exhibited a relatively uniform softening behavior, and, in turn, a relatively broad softening range within the temperatures tested. The material of the present invention ("PLA") exhibited the sharpest softening point) of the tested materials with noticeable deflection occurring above 120 degrees F. Not only did this experiment confirm that the PLA became malleable within a very narrow temperature range, it further confirmed that it would be maintainable in a clinically rigid state below 120 degrees F.

Additional features, advantages, and embodiments of the invention may be set forth or apparent from consideration of the detailed description and drawings. Moreover, it is to be understood that the foregoing summary of the invention and the associated detailed description and drawings are exemplary and intended to provide further explanation without limiting the scope of the invention as claimed.

What is claimed is:

1. A thermoformable medical member and heater comprising:
    a thermoplastic material having a top side and a bottom side opposite the top side, wherein the thermoplastic material comprises a flexural modulus at 73 degrees F.

of at least 2.3 GPa, a heat deflection temperature less than 70 degrees C.; and a thermoformable temperature in the range of 35-70 degrees C.; and a heater operatively associated with at least one of the top and bottom sides of the thermoplastic material, wherein the thermoplastic material contains a polylactic acid (PLA) polymer and the PLA polymer has an L-lactide/D-lactide ratio of 24:1 to 30:1.

2. The invention according to claim 1 wherein the thermoplastic material has a tensile modulus of at least 0.3 GPa at 23 degrees C.

3. The invention according to claim 1 wherein the PLA polymer has a flexural modulus of 2.4-4.9 GPa at 23 degrees C.

4. The invention according to claim 1 wherein the thermoplastic material further includes at least one of an organic and inorganic filler.

5. The invention according to claim 4 wherein the filler has a thermal conductivity greater than 0.12 W/(meter ° C.) at 48 degrees C.

6. The invention according to claim 1 wherein the thermoplastic material has at least a portion of at least one of the top and bottom sides has a textured surface.

7. The invention according to claim 6 wherein the textured surface is corrugated.

8. The invention according to claim 1 wherein the thermoplastic material has an internal structure, having a volume, located between the top and bottom sides, wherein 40% or less of the volume is defined by an open cell structure.

9. The invention according to claim 1 wherein the thermoformable medical member comprises a splint.

10. The invention according to claim 1 wherein the thermoformable medical member comprises an orthotic.

11. The invention according to claim 1 wherein the thermoformable medical member comprises an exoskeleton member.

12. The invention according to claim 1 wherein the heater comprises one of an oxygen activated heater and a water activated heater.

13. The invention according to claim 12 wherein the heater is integrated with the thermoformable medical member.

14. The invention according to claim 1 wherein the thermoplastic material is chemically or physically bonded to the heater.

15. The invention according to claim 1 wherein the thermoplastic material has a glass transition temperature in the range of 35-70 degrees C.

16. The invention according to claim 1 wherein the thermoplastic material contains a reinforcing fiber.

17. The invention according to claim 1 wherein the thermoformable medical member contains a thermosetting component capable of forming crosslinks in the range of 20-70 degrees C.

18. A method for achieving an effect on a thermoformable medical member from an integrated heater for use on a patient comprising the steps of:

heating a thermoformable medical member fabricated from a thermoplastic material with at least one of an oxygen activated heater and a water activated heater in a range of 48-70 degrees C., wherein the thermoplastic material prior to heating is in a relatively rigid, non-thermoformable phase;

converting the thermoplastic material from a non-thermoformable state to a thermoformable state within the heated range;

forming the thermoplastic material to a desired shape while in its thermoformable state;

converting the thermoplastic material back toward and into a relatively rigid non-thermoformable phase; and maintaining the desired shape of the thermoplastic material at a temperature imparted to the thermoplastic material of less than 48 degrees C.

19. The method according to claim 18 wherein the step of converting the thermoplastic material from a non-thermoformable state comprises maintaining structural rigidity of the thermoplastic material until the thermoplastic material until it is heated within the range of 48-70 degrees C.

20. The method according to claim 18 wherein the step of heating comprises constructing the heater so that it ceases to generate heat to the thermoplastic material in the range of 48-70 degrees C. after the thermoplastic material has been converted to a thermoformable state.

21. The method according to claim 20 wherein the step of heating comprises generating heat to the thermoplastic material in the range of 48-70 degrees C. after the thermoplastic material has been converted to a thermoformable state for a period of approximately 1-7 minutes, and, preferably 3-5 minutes.

22. The method according to claim 18 wherein the step of converting the thermoplastic material back toward and into a relatively rigid non-thermoformable state occurs after the temperature of the thermoplastic material is less than 48 degrees C.

23. The method according to claim 22 wherein the step of converting the thermoplastic material back toward and into a relatively rigid non-thermoformable state occurs within 1-7 minutes, and, preferably 3-5 minutes.

24. A thermoformable medical member and heater comprising:

a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and a heater operatively associated with at least one of the top and bottom sides of the thermoplastic material, wherein the thermoplastic material further includes at least one of an organic and inorganic filler.

25. The invention according to claim 24 wherein the thermoplastic material has a tensile modulus of at least 0.3 GPa at 23 degrees C.

26. The invention according to claim 24 wherein the thermoplastic material contains a polylactic acid (PLA) polymer, cellulose acetate butyrate, or polycaprolactone.

27. The invention according to claim 26 wherein the PLA polymer has a flexural modulus of 2.4-4.9 GPa at 23 degrees C.

28. The invention according to claim 24 wherein the thermoplastic material has at least a portion of at least one of the top and bottom sides has a textured surface.

29. The invention according to claim 28 wherein the textured surface is corrugated.

30. The invention according to claim 24 wherein the thermoplastic material has an internal structure, having a volume, located between the top and bottom sides, wherein 40% or less of the volume is defined by an open cell structure.

31. The invention according to claim 24 wherein the thermoformable medical member comprises a splint.

32. The invention according to claim 24 wherein the thermoformable medical member comprises an orthotic.

33. The invention according to claim 24 wherein the thermoformable medical member comprises an exoskeleton member.

34. The invention according to claim 24 wherein the heater comprises one of an oxygen activated heater and a water activated heater.

35. The invention according to claim 34 wherein the heater is integrated with the thermoformable medical member.

36. The invention according to claim 24 wherein the thermoplastic material is chemically or physically bonded to the heater.

37. The invention according to claim 24 wherein the thermoplastic material has a glass transition temperature in the range of 35-70 degrees C.

38. The invention according to claim 24 wherein the thermoplastic material contains a reinforcing fiber.

39. The invention according to claim 24 wherein the thermoformable medical member contains a thermosetting component capable of forming crosslinks in the range of 20-70 degrees C.

40. A thermoformable medical member and heater comprising:
a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and
a heater operatively associated with at least one of the top and bottom sides of the thermoplastic material,
wherein the thermoplastic material further includes at least one of an organic and inorganic filler, and the filler has a thermal conductivity greater than 0.12 W/(meter ° C.) at 48 degrees C.

41. The invention according to claim 40 wherein the thermoplastic material has a tensile modulus of at least 0.3 GPa at 23 degrees C.

42. The invention according to claim 40 wherein the thermoplastic material contains a polylactic acid (PLA) polymer, cellulose acetate butyrate, or polycaprolactone.

43. The invention according to claim 42 wherein the PLA polymer has a flexural modulus of 2.4-4.9 GPa at 23 degrees C.

44. The invention according to claim 40 wherein the thermoplastic material has at least a portion of at least one of the top and bottom sides has a textured surface.

45. The invention according to claim 44 wherein the textured surface is corrugated.

46. The invention according to claim 40 wherein the thermoplastic material has an internal structure, having a volume, located between the top and bottom sides, wherein 40% or less of the volume is defined by an open cell structure.

47. The invention according to claim 40 wherein the thermoformable medical member comprises a splint.

48. The invention according to claim 40 wherein the thermoformable medical member comprises an orthotic.

49. The invention according to claim 40 wherein the thermoformable medical member comprises an exoskeleton member.

50. The invention according to claim 40 wherein the heater comprises one of an oxygen activated heater and a water activated heater.

51. The invention according to claim 50 wherein the heater is integrated with the thermoformable medical member.

52. The invention according to claim 40 wherein the thermoplastic material is chemically or physically bonded to the heater.

53. The invention according to claim 40 wherein the thermoplastic material has a glass transition temperature in the range of 35-70 degrees C.

54. The invention according to claim 40 wherein the thermoplastic material contains a reinforcing fiber.

55. The invention according to claim 40 wherein the thermoformable medical member contains a thermosetting component capable of forming crosslinks in the range of 20-70 degrees C.

56. A thermoformable medical member and heater comprising:
a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and
a heater operatively associated with at least one of the top and bottom sides of the thermoplastic material,
wherein the thermoplastic material has at least a portion of at least one of the top and bottom sides has a textured surface.

57. The invention according to claim 56 wherein the thermoplastic material has a tensile modulus of at least 0.3 GPa at 23 degrees C.

58. The invention according to claim 56 wherein the thermoplastic material contains a polylactic acid (PLA) polymer, cellulose acetate butyrate, or polycaprolactone.

59. The invention according to claim 58 wherein the PLA polymer has a flexural modulus of 2.4-4.9 GPa at 23 degrees C.

60. The invention according to claim 56 wherein the thermoplastic material has an internal structure, having a volume, located between the top and bottom sides, wherein 40% or less of the volume is defined by an open cell structure.

61. The invention according to claim 56 wherein the thermoformable medical member comprises a splint.

62. The invention according to claim 56 wherein the thermoformable medical member comprises an orthotic.

63. The invention according to claim 56 wherein the thermoformable medical member comprises an exoskeleton member.

64. The invention according to claim 56 wherein the heater comprises one of an oxygen activated heater and a water activated heater.

65. The invention according to claim 64 wherein the heater is integrated with the thermoformable medical member.

66. The invention according to claim 56 wherein the thermoplastic material is chemically or physically bonded to the heater.

67. The invention according to claim 56 wherein the thermoplastic material has a glass transition temperature in the range of 35-70 degrees C.

68. The invention according to claim 56 wherein the thermoplastic material contains a reinforcing fiber.

69. The invention according to claim 56 wherein the thermoformable medical member contains a thermosetting component capable of forming crosslinks in the range of 20-70 degrees C.

70. A thermoformable medical member and heater comprising:

a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and a heater operatively associated with at least one of the top and bottom sides of the thermoplastic material, wherein the thermoplastic material has at least a portion of at least one of the top and bottom sides has a textured surface, and the textured surface is corrugated.

71. The invention according to claim 70 wherein the thermoplastic material has a tensile modulus of at least 0.3 GPa at 23 degrees C.

72. The invention according to claim 70 wherein the thermoplastic material contains a polylactic acid (PLA) polymer, cellulose acetate butyrate, or polycaprolactone.

73. The invention according to claim 72 wherein the PLA polymer has a flexural modulus of 2.4-4.9 GPa at 23 degrees C.

74. The invention according to claim 70 wherein the thermoplastic material has an internal structure, having a volume, located between the top and bottom sides, wherein 40% or less of the volume is defined by an open cell structure.

75. The invention according to claim 70 wherein the thermoformable medical member comprises a splint.

76. The invention according to claim 70 wherein the thermoformable medical member comprises an orthotic.

77. The invention according to claim 70 wherein the thermoformable medical member comprises an exoskeleton member.

78. The invention according to claim 70 wherein the heater comprises one of an oxygen activated heater and a water activated heater.

79. The invention according to claim 78 wherein the heater is integrated with the thermoformable medical member.

80. The invention according to claim 70 wherein the thermoplastic material is chemically or physically bonded to the heater.

81. The invention according to claim 70 wherein the thermoplastic material has a glass transition temperature in the range of 35-70 degrees C.

82. The invention according to claim 70 wherein the thermoplastic material contains a reinforcing fiber.

83. The invention according to claim 70 wherein the thermoformable medical member contains a thermosetting component capable of forming crosslinks in the range of 20-70 degrees C.

84. A thermoformable medical member and heater comprising:

a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and a heater operatively associated with at least one of the top and bottom sides of the thermoplastic material, wherein the thermoplastic material has an internal structure, having a volume, located between the top and bottom sides, wherein 40% or less of the volume is defined by an open cell structure.

85. The invention according to claim 84 wherein the thermoplastic material has a tensile modulus of at least 0.3 GPa at 23 degrees C.

86. The invention according to claim 84 wherein the thermoplastic material contains a polylactic acid (PLA) polymer, cellulose acetate butyrate, or polycaprolactone.

87. The invention according to claim 86 wherein the PLA polymer has a flexural modulus of 2.4-4.9 GPa at 23 degrees C.

88. The invention according to claim 84 wherein the thermoformable medical member comprises a splint.

89. The invention according to claim 84 wherein the thermoformable medical member comprises an orthotic.

90. The invention according to claim 84 wherein the thermoformable medical member comprises an exoskeleton member.

91. The invention according to claim 84 wherein the heater comprises one of an oxygen activated heater and a water activated heater.

92. The invention according to claim 91 wherein the heater is integrated with the thermoformable medical member.

93. The invention according to claim 84 wherein the thermoplastic material is chemically or physically bonded to the heater.

94. The invention according to claim 84 wherein the thermoplastic material has a glass transition temperature in the range of 35-70 degrees C.

95. The invention according to claim 84 wherein the thermoplastic material contains a reinforcing fiber.

96. The invention according to claim 84 wherein the thermoformable medical member contains a thermosetting component capable of forming crosslinks in the range of 20-70 degrees C.

97. A thermoformable medical member and heater comprising:

a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and a heater operatively associated with at least one of the top and bottom sides of the thermoplastic material, wherein the heater comprises one of an oxygen activated heater and a water activated heater.

98. The invention according to claim 97 wherein the thermoplastic material has a tensile modulus of at least 0.3 GPa at 23 degrees C.

99. The invention according to claim 97 wherein the thermoplastic material contains a polylactic acid (PLA) polymer, cellulose acetate butyrate, or polycaprolactone.

100. The invention according to claim 99 wherein the PLA polymer has a flexural modulus of 2.4-4.9 GPa at 23 degrees C.

101. The invention according to claim 97 wherein the thermoformable medical member comprises a splint.

102. The invention according to claim 97 wherein the thermoformable medical member comprises an orthotic.

103. The invention according to claim 97 wherein the thermoformable medical member comprises an exoskeleton member.

104. The invention according to claim 97 wherein the thermoplastic material is chemically or physically bonded to the heater.

105. The invention according to claim 97 wherein the thermoplastic material has a glass transition temperature in the range of 35-70 degrees C.

106. The invention according to claim 97 wherein the thermoplastic material contains a reinforcing fiber.

107. The invention according to claim 97 wherein the thermoformable medical member contains a thermosetting component capable of forming crosslinks in the range of 20-70 degrees C.

108. A thermoformable medical member and heater comprising:
a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and
a heater operatively associated with at least one of the top and bottom sides of the thermoplastic material,
wherein the heater comprises one of an oxygen activated heater and a water activated heater and the heater is integrated with the thermoformable medical member.

109. The invention according to claim 108 wherein the thermoplastic material has a tensile modulus of at least 0.3 GPa at 23 degrees C.

110. The invention according to claim 108 wherein the thermoplastic material contains a polylactic acid (PLA) polymer, cellulose acetate butyrate, or polycaprolactone.

111. The invention according to claim 110 wherein the PLA polymer has a flexural modulus of 2.4-4.9 GPa at 23 degrees C.

112. The invention according to claim 108 wherein the thermoformable medical member comprises a splint.

113. The invention according to claim 108 wherein the thermoformable medical member comprises an orthotic.

114. The invention according to claim 108 wherein the thermoformable medical member comprises an exoskeleton member.

115. The invention according to claim 108 wherein the thermoplastic material is chemically or physically bonded to the heater.

116. The invention according to claim 108 wherein the thermoplastic material has a glass transition temperature in the range of 35-70 degrees C.

117. The invention according to claim 108 wherein the thermoplastic material contains a reinforcing fiber.

118. The invention according to claim 108 wherein the thermoformable medical member contains a thermosetting component capable of forming crosslinks in the range of 20-70 degrees C.

119. A thermoformable medical member and heater comprising:
a thermoplastic material having a top side and a bottom side opposite the top side, wherein the thermoplastic material comprises a flexural modulus at 73 degrees F. of at least 2.3 GPa, a heat deflection temperature less than 70 degrees C.; and a thermoformable temperature in the range of 35-70 degrees C.; and
a heater operatively associated with at least one of the top and bottom sides of the thermoplastic material,
wherein the thermoplastic material contains a reinforcing fiber.

120. The invention according to claim 119 wherein the thermoplastic material has a tensile modulus of at least 0.3 GPa at 23 degrees C.

121. The invention according to claim 119 wherein the thermoplastic material contains a polylactic acid (PLA) polymer, cellulose acetate butyrate, or polycaprolactone.

122. The invention according to claim 121 wherein the PLA polymer has a flexural modulus of 2.4-4.9 GPa at 23 degrees C.

123. The invention according to claim 119 wherein the thermoformable medical member comprises a splint.

124. The invention according to claim 119 wherein the thermoformable medical member comprises an orthotic.

125. The invention according to claim 119 wherein the thermoformable medical member comprises an exoskeleton member.

126. The invention according to claim 119 wherein the thermoplastic material is chemically or physically bonded to the heater.

127. The invention according to claim 119 wherein the thermoplastic material has a glass transition temperature in the range of 35-70 degrees C.

128. The invention according to claim 119 wherein the thermoformable medical member contains a thermosetting component capable of forming crosslinks in the range of 20-70 degrees C.

* * * * *